US008525675B2

(12) United States Patent
Zhang et al.

(10) Patent No.: US 8,525,675 B2
(45) Date of Patent: Sep. 3, 2013

(54) SECURITY DEVICE

(75) Inventors: Ningsheng Zhang, Charlotte, NC (US); Brian V. Conti, Matthews, NC (US)

(73) Assignee: Checkpoint Systems, Inc.

( * ) Notice: Subject to any disclaimer, the term of this patent is extended or adjusted under 35 U.S.C. 154(b) by 0 days.

(21) Appl. No.: 13/372,690

(22) Filed: Feb. 14, 2012

(65) Prior Publication Data

US 2012/0152883 A1 Jun. 21, 2012

Related U.S. Application Data

(63) Continuation-in-part of application No. 12/723,326, filed on Mar. 12, 2010.

(51) Int. Cl.
*G08B 13/14* (2006.01)
*A61J 1/00* (2006.01)

(52) U.S. Cl.
USPC .......................... 340/568.1; 340/571; 215/201

(58) Field of Classification Search
USPC ........... 340/573.1, 568.1, 540, 571; 215/201, 215/207, 215, 230, 302
See application file for complete search history.

(56) References Cited

U.S. PATENT DOCUMENTS

| | | | | |
|---|---|---|---|---|
| 5,957,313 | A * | 9/1999 | Bouan | 215/215 |
| 6,769,557 | B2 | 8/2004 | Michael et al. | |
| 6,822,567 | B2 | 11/2004 | Durbin | |
| 7,100,783 | B2 | 9/2006 | Belden, Jr. | |
| 7,259,674 | B2 * | 8/2007 | Marsilio et al. | 340/572.1 |
| 7,372,363 | B2 | 5/2008 | Durbin | |
| 2004/0163430 | A1 | 8/2004 | Belden, Jr. | |
| 2005/0017865 | A1 | 1/2005 | Belden, Jr. | |
| 2005/0237205 | A1 | 10/2005 | Gorst | |
| 2006/0170559 | A1 | 8/2006 | Marsilio et al. | |
| 2009/0152230 | A1 | 6/2009 | Belden, Jr. | |
| 2009/0223260 | A1 | 9/2009 | Conti et al. | |
| 2011/0219828 | A1 | 9/2011 | Zhang et al. | |
| 2011/0241849 | A1 | 10/2011 | Jacobs et al. | |

FOREIGN PATENT DOCUMENTS

| | | |
|---|---|---|
| FR | 2735751 | 12/1996 |
| WO | 0175254 | 10/2001 |
| WO | 2006033123 | 3/2006 |
| WO | 2008075310 | 6/2008 |

* cited by examiner

*Primary Examiner* — Anh V La

(57) ABSTRACT

An anti-theft security device is particularly useful with bottles and is typically secured to a bottle neck. The device may carry an onboard alarm. The device typically includes a catch member which engages the bottle neck to secure the device to the bottle and a blocking structure to help block access to the catch member.

34 Claims, 9 Drawing Sheets

| |
|---|
| FIG-2A |
| FIG-2B |
| FIG-2C |

SECURITY DEVICE

CROSS-REFERENCE TO RELATED APPLICATION

This application is a continuation-in-part of U.S. patent application Ser. No. 12/723,326, filed Mar. 12, 2010; the disclosure of which is incorporated herein by reference.

BACKGROUND OF THE INVENTION

1. Technical Field

The present invention relates generally to security devices for preventing theft of merchandise. More particularly, the present invention relates to a bottle security device configured to be secured to a bottle in order to prevent theft of the bottle and contents thereof. Specifically, the bottle security device of the present invention provides an improved securing mechanism and may carry an onboard alarm.

2. Background Information

A great number of bottle security devices have been configured for securing to a bottle in order to deter the theft of the bottle and contents thereof. Most of these bottle security devices are secured to the neck of a bottle, and some of them are configured to not only prevent the removal of the bottle from a store, but are also configured to cover the closure of the bottle in order to prevent removal of the contents of the bottle while inside the store. Most of the modern devices include an EAS tag so that as a potential thief attempts to leave a store with the bottle, a gate alarm is set off as the EAS tag approaches a gate of the security system within the store. However, bottle security devices have not heretofore been configured to carry an onboard alarm. In addition, there is always a need in the art for new securing mechanisms to help defeat unauthorized removal of the bottle security device from the bottle. The present invention addresses these and other issues.

BRIEF SUMMARY OF THE INVENTION

The present invention provides a bottle security device comprising a base; a securing mechanism mounted on the base and having a securing position adapted to secure the device to the bottle and an unsecured position adapted to allow the device to be removed from the bottle; and an onboard audible alarm.

The present invention also provides a bottle security device comprising a sleeve defining an upper cavity and a lower cavity having a bottom entrance opening; the lower cavity adapted to receive a bottle neck through the bottom entrance opening; a shelf which separates the upper and lower cavities; a speaker in the upper cavity; a speaker hole formed through the shelf; and an open sound pathway from the speaker to the bottom entrance opening extending from the speaker through the speaker hole and lower cavity.

The present invention further provides a combination comprising a bottle; a bottle security device secured to the bottle; and an audible alarm carried by the bottle security device.

BRIEF DESCRIPTION OF THE SEVERAL VIEWS OF THE DRAWINGS

A preferred embodiment of the invention, illustrated of the best mode in which Applicant contemplates applying the principles, is set forth in the following description and is shown in the drawings and is particularly and distinctly pointed out and set forth in the appended claims.

Similar numbers refer to similar parts throughout the drawings.

DETAILED DESCRIPTION OF THE INVENTION

Figures 1, 2:
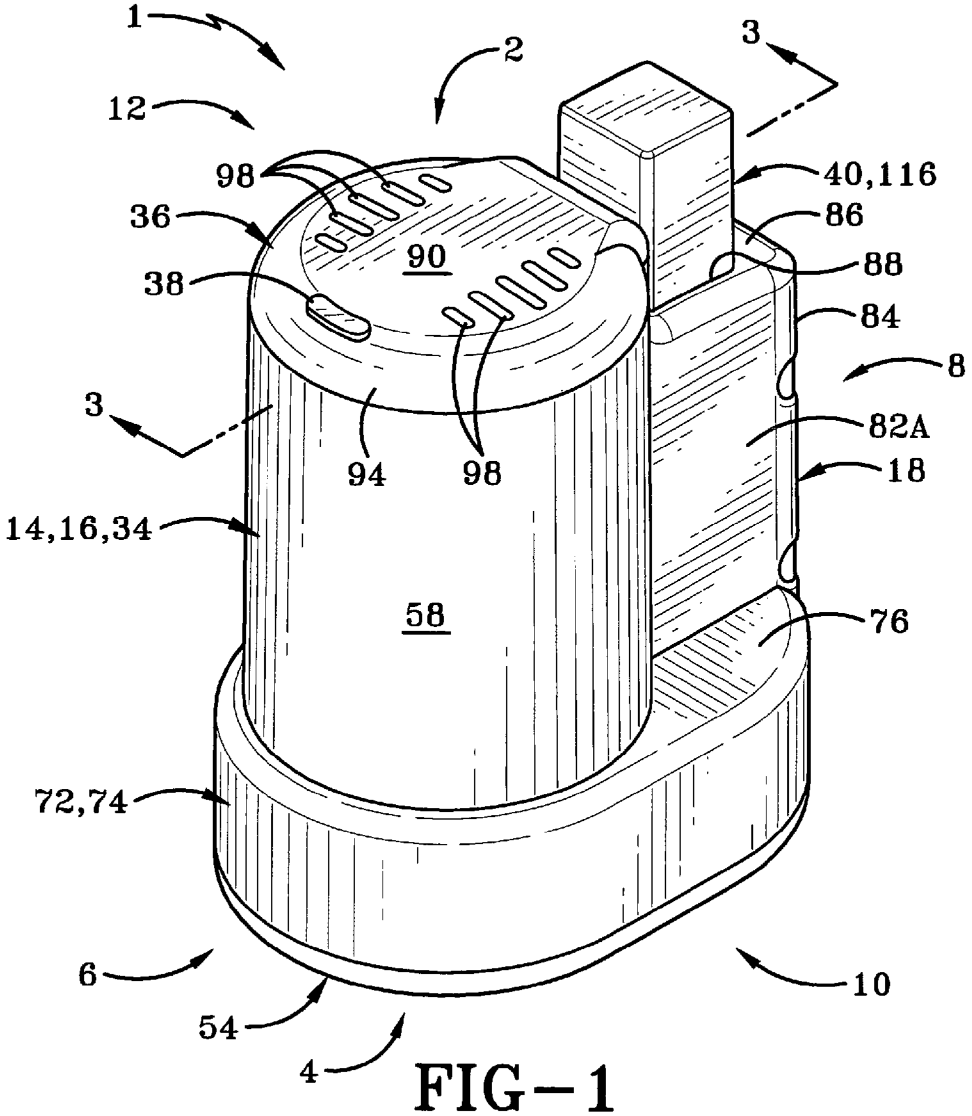
FIG. 1 is a perspective view of the bottle security device of the present invention.
FIG. 2 is a diagrammatic view showing the orientation of FIGS. 2A, 2B and 2C relative to one another.
Figure 3:
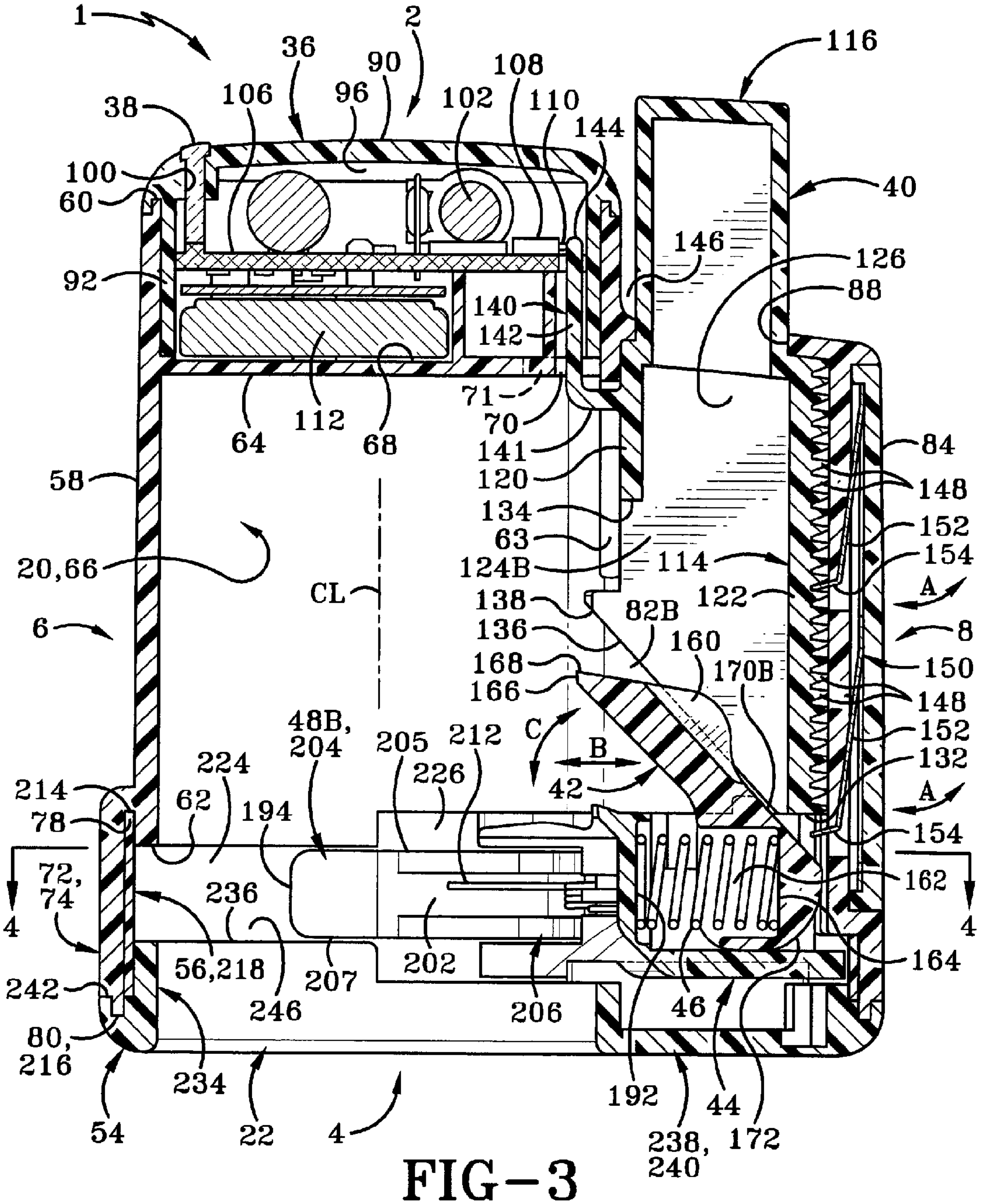
FIG. 3 is a sectional view taken on line 3-3 of FIG. 1 midway between the left and right sides of the bottle security device showing the device in the unsecured position.

The bottle security device of the present invention is shown generally at 1 in FIG. 1. Device 1 is shown in an upright orientation and has a top 2, a bottom 4, a front 6, a back 8, a left side 10 and a right side 12. Device 1 includes a rigid base 14 which is typically formed of a rigid plastic material and includes a sleeve 16 which defines the front of the device, and a housing 18 the front of which is rigidly secured to the back of sleeve 16 and extends rearwardly therefrom to the back the device. As shown in FIG. 3, sleeve 16 defines a bottleneck receiving sleeve cavity or interior chamber 20 which is closed at its top and has a bottom entrance opening 22 at bottom 4. Cavity 20 is configured to receive therein via bottom entrance opening 22 a bottleneck 24 (FIG. 5) of a bottle 26 which is shown in an upright orientation. Neck 24 typically includes a narrow neck portion 28, an annular shoulder or flange 30 which extends radially outwardly from the top of neck portion 28, and a closure 32 such as a screw-on cap, cork or the like for closing the bottle to retain the contents thereof.

Figure 2A:
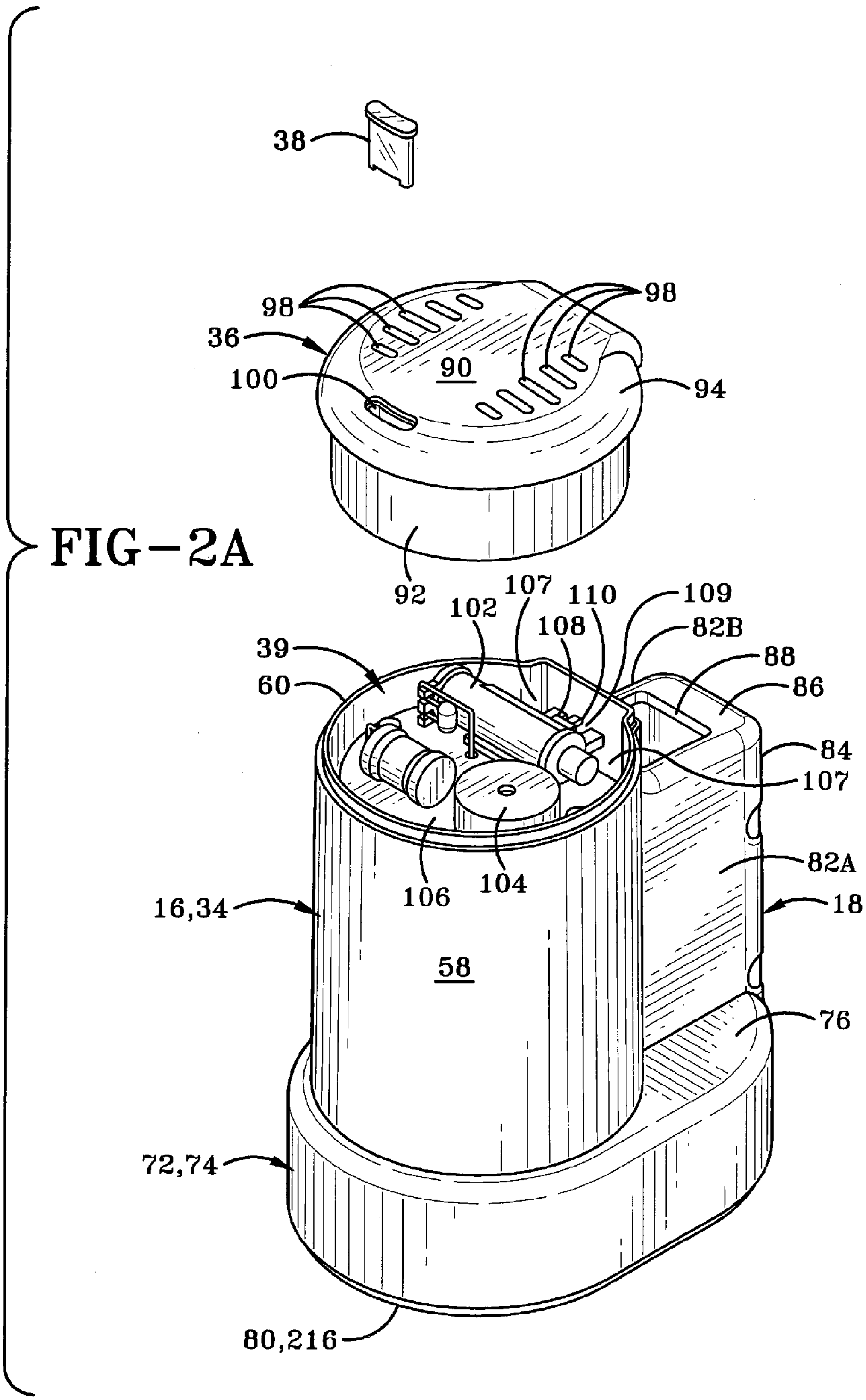
FIG. 2A is an exploded perspective view showing the light pipe, the top member of the base, and the primary member of the base with the alarm system seated in the upper portion of the primary member.
Figure 2B:
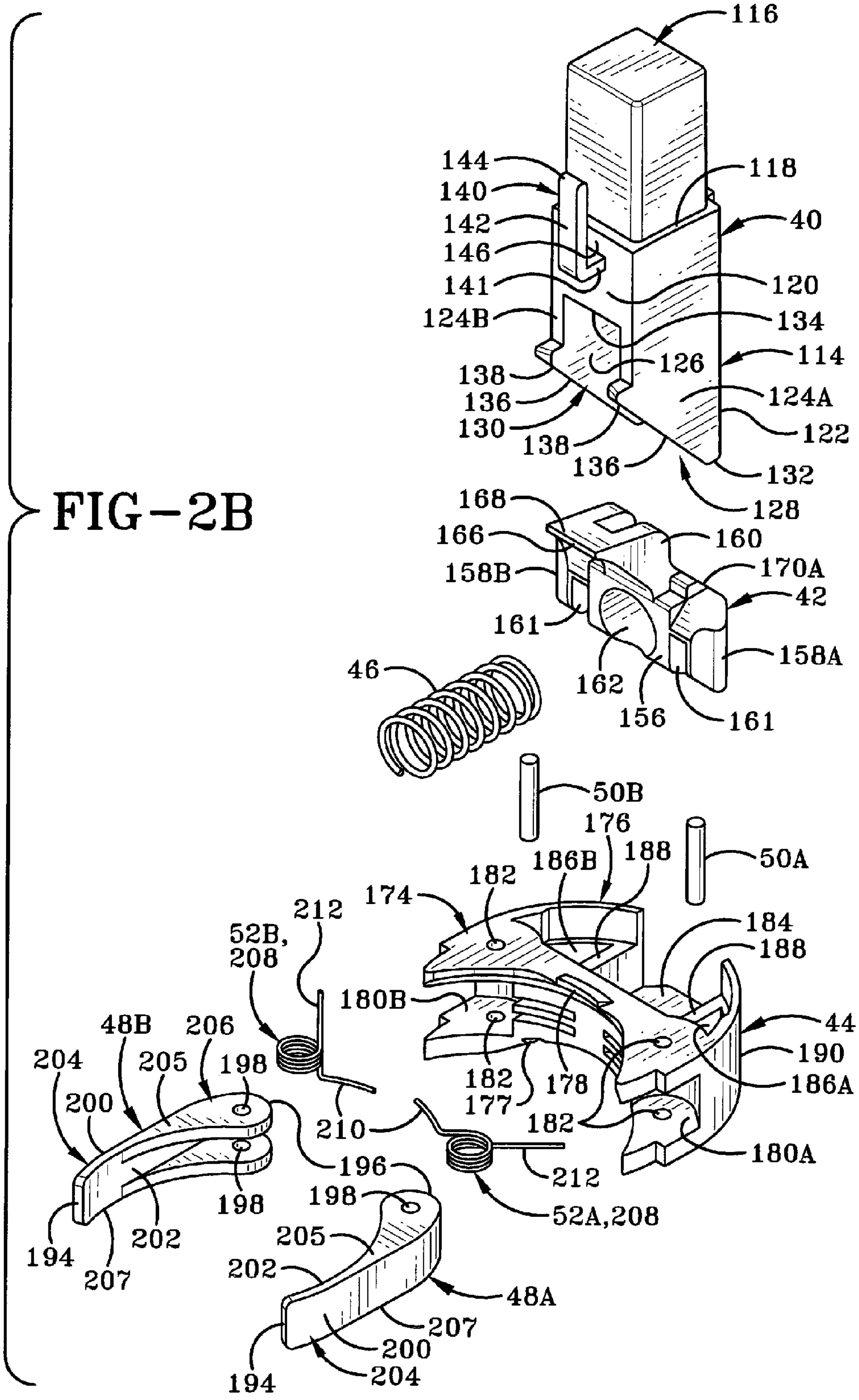
FIG. 2B is an exploded perspective view of various components of the securing mechanism.
Figure 2C:
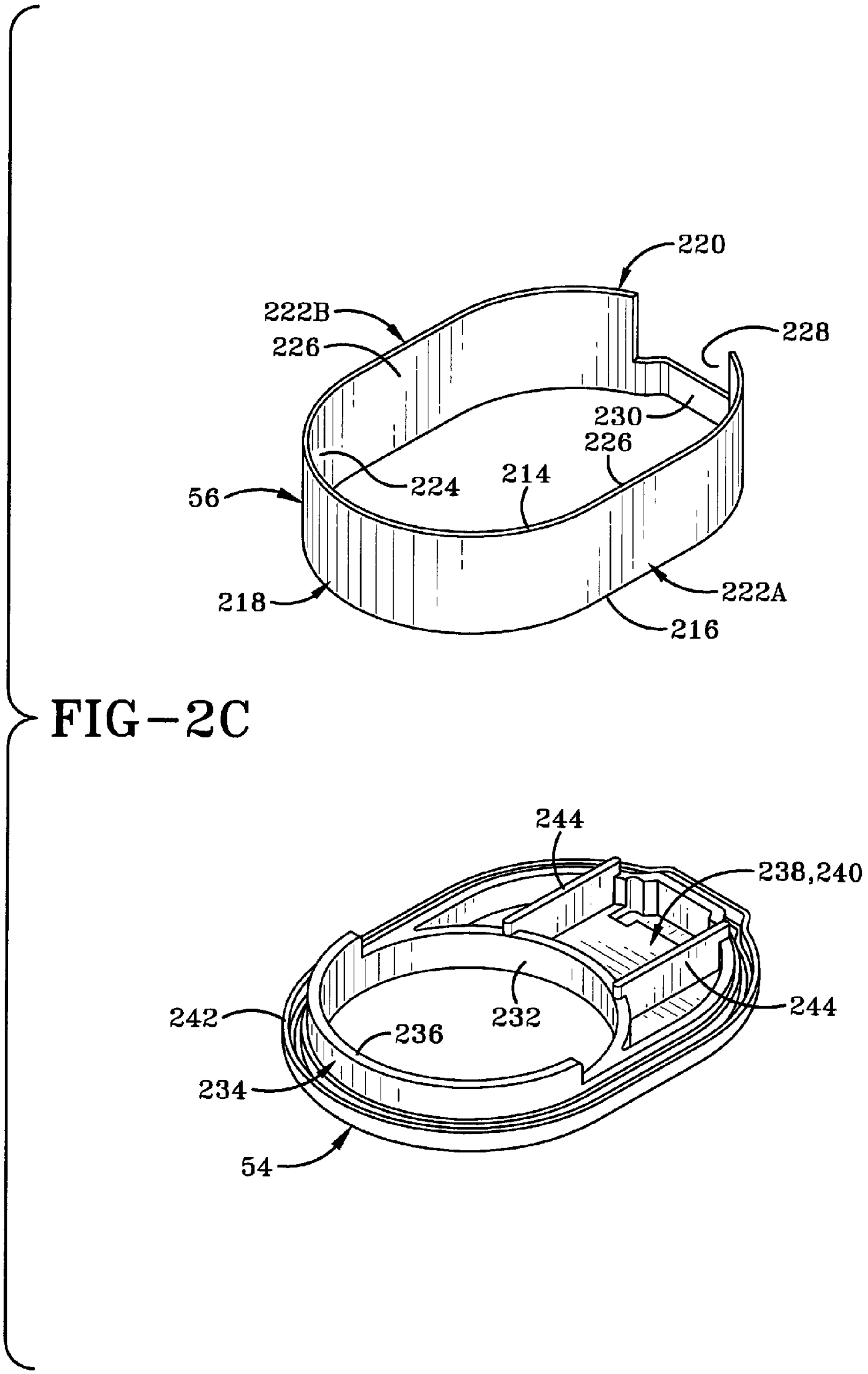
FIG. 2C is an exploded perspective view of the bottom member of the base and the annular insert of the base.

With primary reference to FIGS. 2A, 2B and 2C, device 1 includes a rigid primary member 34 of the base, a rigid top member or cover 36 of the base, a rigid light pipe 38, an alarm system 39 including an onboard audible alarm, a rigid actuating member 40, a rigid cam member or catch member 42, a rigid blocking member 44, a blocking member spring 46, rigid left and right blocking arms 48A and 48B, rigid left and right hinge pins 50A and 50B, left and right blocking arm springs 52A and 52B, a rigid bottom member or cover 54 of the base, and an annular insert 56 of the base. Primary member 34, top cover 36, actuating member 40, catch member 42, blocking member 44, blocking arms 48, bottom cover 54 and insert 56 are in the exemplary embodiment formed of a rigid plastic material while hinge pins 50 are typically formed of metal. As shown in FIG. 1, top cover 36 is rigidly and permanently secured to the top of sleeve 16 such as by sonic welding, glue or any other suitable securing mechanism. Bottom cover 54 is likewise rigidly secured and permanently secured to the bottom of primary member 34.

With primary reference to FIGS. 2A and 3, primary member 34 is described in greater detail. Primary member 34 includes an annular side wall which is substantially cylindrical and may be frustoconical in shape such that the top of the side wall is somewhat narrower than the bottom thereof. Side wall 58 has a substantially circular annular top edge 60 and a bottom edge 62 (FIG. 3) which serves as a downwardly facing ledge which in the exemplary embodiment is semicircular as viewed from below. Member 34 further includes a laterally extending flat horizontal wall or shelf 64 which is substantially circular as viewed from below and in the exemplary embodiment located about three-quarters away up from the bottom and about a quarter of the way down from top 60. Shelf 64 at its circular outer perimeter is rigidly connected to the circular inner surface of side wall 58 and it extends substantially continuously from the front to the back and from the left to the right of side wall 58. Side wall 58 and shelf 64 define there below a lower cavity 66 which opens downwardly and forms a majority of cavity 20. Side wall 58 and shelf 64 define there above an upwardly opening cavity 68 having a top entrance opening defined by top 60. Shelf 64 thus divides or separates the cavity defined by sidewall 58 into lower cavity 66 and upper cavity 68. A through hole or opening 70 is formed through shelf 64 adjacent the rear thereof extending from the bottom to the top of the shelf. On the left and right sides of opening 70 are additional openings 71 (FIGS. 3, 4) likewise extending from the top to the bottom of shelf 64. Openings 70 and 71 thus form respective passages extending between and communicating with the top rear of cavity 66 and the bottom rear of cavity 68. Openings 70 and 71 serve as speaker holes while opening 70 provides an additional purpose discussed further below. Side wall 58 defines a generally rectangular rear opening 63 formed in the back portion of side wall 58 whereby housing cavity 24 communicates with cavities 20 and 66. The top of through opening 63 is adjacent the rear of shelf 64 and openings 70 and 71. The bottom of opening 63 is at or adjacent the bottom of side wall 58.

Member 34 further includes a generally oval skirt 72 which is rigidly secured to side wall 58 adjacent its lower end and extends radially outwardly and downwardly therefrom. Skirt 72 includes an annular skirt side wall 74 which is semicircular on the front portion, semicircular on the rear portion and includes straight left and right portions which interconnect the semicircular portions. Skirt 72 further includes a flat skirt top wall 76 which is substantially horizontal and is rigidly connected at a circular inner perimeter to the circular outer perimeter of side wall 58 adjacent bottom 62 and spaced upwardly therefrom a short distance. Top wall 76 extends outwardly to a rigid generally oval outer perimeter and connection to the top of skirt side wall 74, which extends downwardly therefrom. The front half of bottom portion of side wall 58 and the front semicircular upper portion of side wall 74 define therebetween a U-shaped semicircular slot 78 which opens downwardly at a bottom entrance opening at bottom 62. Skirt side wall 74 thus has an annular generally oval bottom 80 which is spaced downwardly from bottom 62 and is adjacent bottom 4 of device 1.

Housing 18 includes left and right flat vertical rectangular side walls 82A and 82B which are rigidly secured at their front ends to the rear of side wall 58 and extend rearwardly therefrom. Housing 18 further includes a flat rectangular back wall which is perpendicular to the parallel side walls 82 and is rigidly secured at its left edge to the back edge of left side wall 82A and at its right edge to the back edge of right side wall 82B. Housing 18 further includes an annular substantially horizontal flat top wall 86 which is generally square as viewed from above and is rigidly secured to the top edges of walls 82A, 82B and 84 and also to the back of side wall 58. Top wall 86 defines a square through hole 88 extending from top to the bottom of wall 86 and providing a top entrance opening of housing cavity 24 rearward of and adjacent the back of side wall 58. The bottoms of side walls 82A and 82B are rigidly secured to skirt top wall 76.

With continued reference to FIGS. 2A and 3, top cover 36 includes a substantially flat horizontal circular top wall 90 and an annular cylindrical side wall 92 which is secured at its top to the bottom of top wall 90 and extends downwardly therefrom to an annular circular bottom edge. Top wall 90 includes along its outer perimeter an annular lip 94 which extends radially outwardly from the top of side wall 92. A speaker grille comprising a plurality of speaker through holes 98 are formed in top wall 90 extending from the top to the bottom thereof whereby holes 100 communicate with cavity 96 and the exterior surface of device 1. Top wall 90 further defines a light pipe receiving through hole 100 for receiving therein light pipe 38. Light pipe 38 is formed of a translucent or transparent material and is received in hole 100 with the top thereof externally exposed along the top surface of wall 90 and the bottom thereof received within cavity 96. As shown in FIGS. 1 and 3, top cover 36 is rigidly secured to the top of sleeve 16 by a rigid connection between lip 94 and top 60 of side wall 58. Side wall 92 is slightly smaller than side wall 58 adjacent the top thereof so that side wall 92 is received within upper cavity 68 with the circular outer surface of side wall 92 adjacent or abutting the circular inner surface of the top portion of side wall 58 and the bottom of side wall 92 adjacent or in contact with shelf 64. Shelf 64 thus substantially closes the bottom entrance opening of cavity 96, whereby top wall 90, side wall 92 and shelf 64 define there within an enclosed interior chamber in which is disposed alarm system 39. Although this upper interior chamber is substantially nearly enclosed in its entirety, the openings which serve as speaker openings, namely upper speaker holes 98 and lower speaker holes 70 and 71, are the exception to the chamber being fully enclosed.

Figure 4:
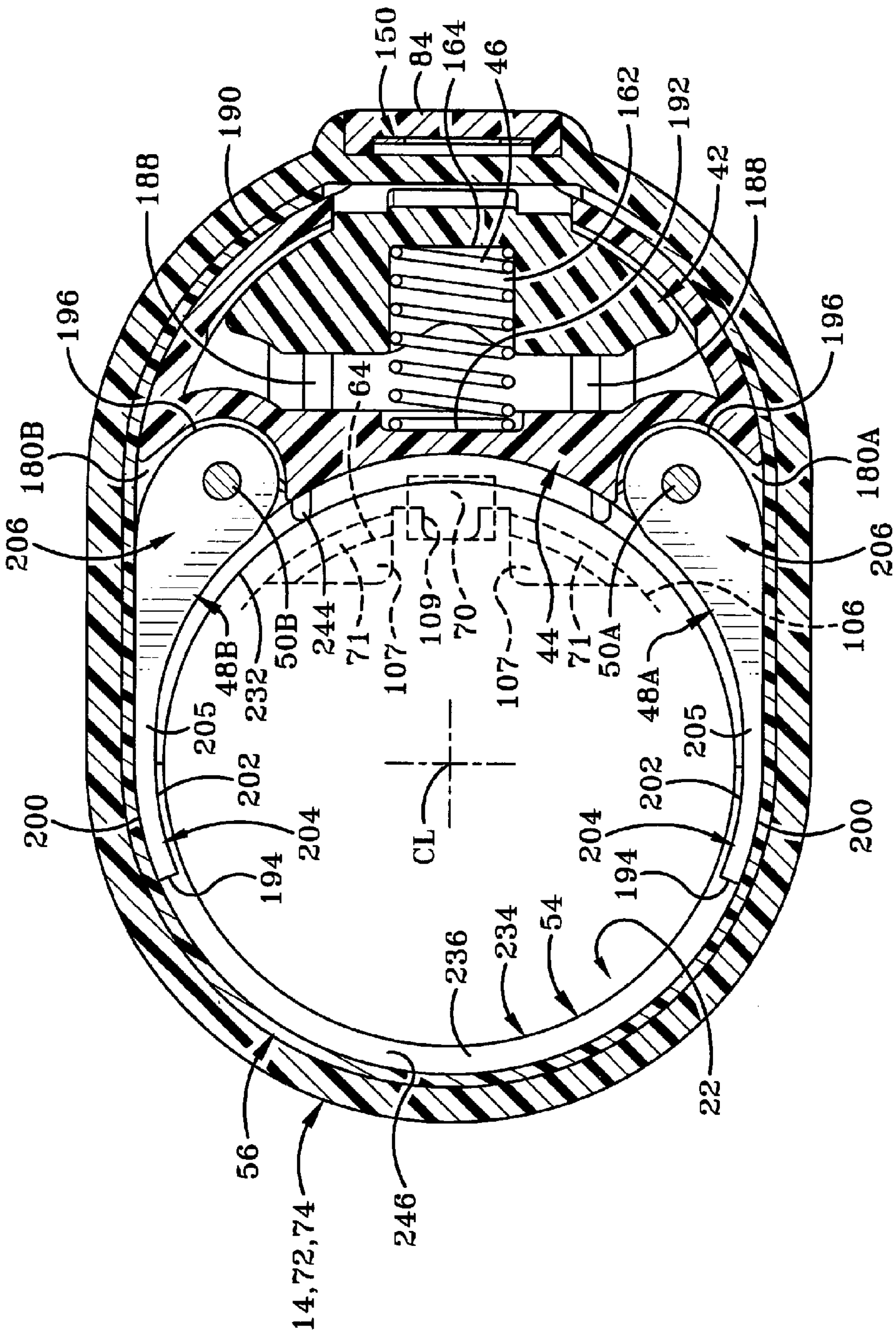
FIG. 4 is a sectional view taken on line 4-4 of FIG. 3 looking downward at portions of the securing mechanism and further showing in phantom speaker holes in members which are above line 4-4.
Figure 5:
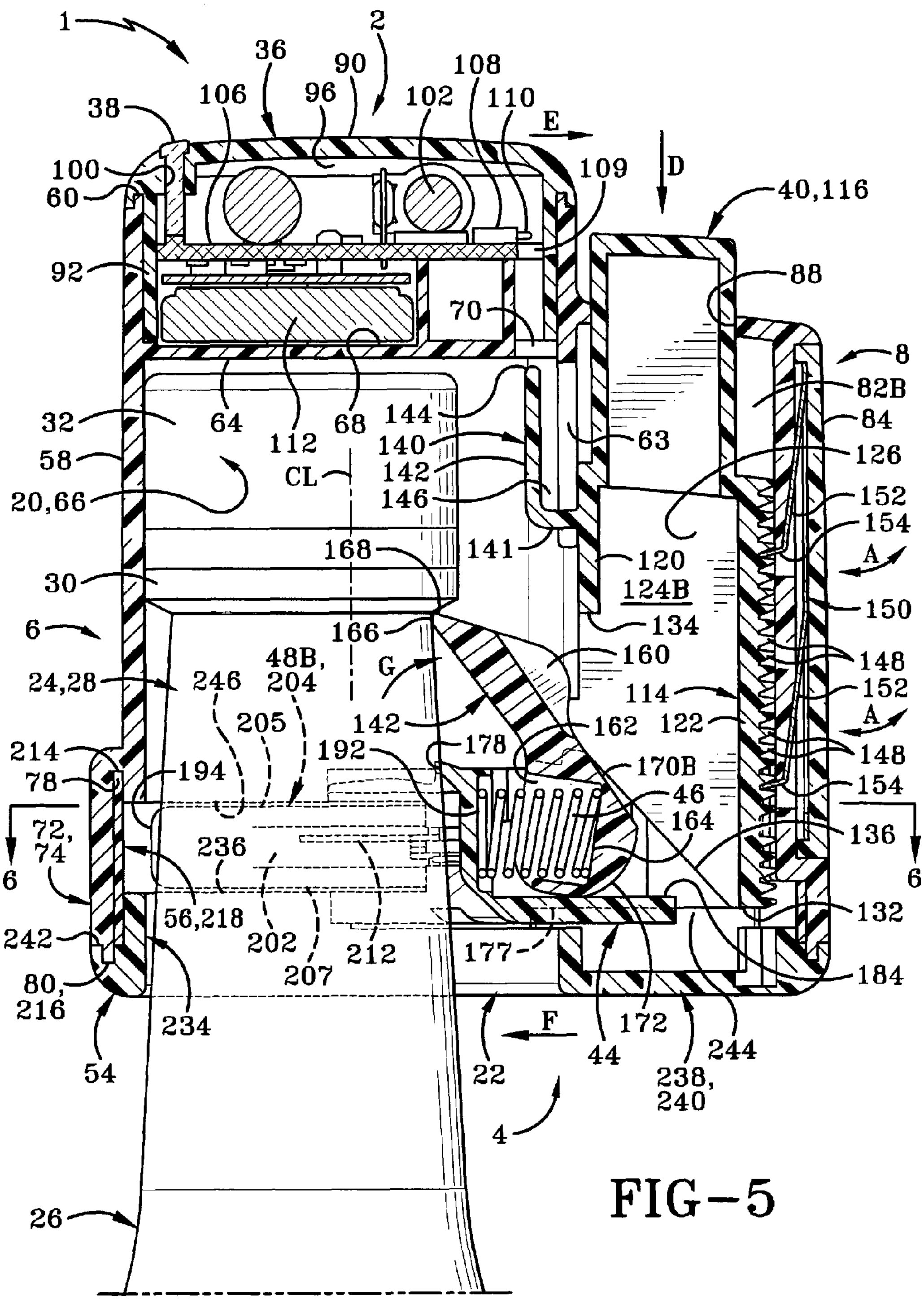
FIG. 5 is similar to FIG. 3 and shows a bottleneck inserted into the sleeve of the device with the securing mechanism in the secured position.

Alarm system 39 includes an EAS tag 102, a speaker 104, a circuit board 106, an arming switch 108 having a switch arm 110, and a battery 112 which is in electrical communication with speaker 104, the circuitry of board 106 and switch 108 to provide electrical power to the circuit board and speaker. Circuit board 106 further includes a light or LED for shining light when turned on directed at and through light pipe 38. Circuit board also defines a pair of through holes 107 respectively to the left and right of another through hole 109. Holes 107 are directly above holes 71, and hole 109 is directly above hole 70 (FIGS. 4, 5). Switch arm 110 has first and second positions in which any electrical arming circuit of circuit board 106 is respectively opened and closed whereby one of the opened and closed positions is an armed position and the other is a disarmed position. Alarm system thus includes an onboard audible alarm which does not include EAS tag 102. Top speaker holes 98 are above or higher than speaker 104 whereas lower holes 70, 71 are below or lower than speaker 104.

Device 1 includes an open sound pathway from speaker 104 to the exterior surface of device 1 wherein the open sound pathway includes speaker holes 98, whereby this open pathway extends from speaker 104 through space above the circuit board and upwardly therefrom through speaker holes 98, which provide an upwardly opening sound exit opening of the pathway to the exterior of device 1. Thus, when the onboard alarm is activated, sound emitted from speaker 104 is directed along this pathway through space above the circuit board and upwardly through the sound exit opening provided by speaker holes 98 at the top of device 1 so that sound emitted from speaker 104 is directed upwardly through speaker holes 98.

Device 1 also includes another open sound pathway from speaker 104 to the exterior surface of device 1 wherein this second open pathway includes a downwardly opening sound exit opening which opens downwardly at the bottom of device 1 so that sound emitted from speaker 104 is directed downwardly from device when the onboard alarm is activated. More particularly, this second open pathway includes speaker holes 70, 71, 107 and 109 whereby the second open pathway extends from speaker 104 through space above the circuit board and downwardly therefrom through holes 107 and 109 and further downwardly therefrom through speaker holes 70 and 71 and further downwardly into sleeve cavity 20 to entrance opening 22. Thus, this second open pathway is configured to direct sound emitted from speaker 104 downwardly through speaker holes 107 and 109 to and through speaker holes 70 and 71 and further downwardly into sleeve cavity 20 to exit downwardly therefrom at entrance opening 22, which serves as a bottom sound exit opening through which sound emitted from speaker 104 is directed downwardly to the exterior of device 1. When device 1 is secured to bottle 26 (FIGS. 5-6), the second sound pathway extends around the outer surface of bottle neck 24 and also around portions of blocking member 44 and blocking arms 48. The second sound exit opening may extend between each arm 48 and bottle neck 24 and also between each arm 48 and each of insert 56 and sleeve sidewall 58, 232.

With reference to FIGS. 2B and 3, actuating member 40 includes a lower portion 114 and an upper portion 116 each of which is substantially square as viewed from above. Upper portion 116 serves as a button and is generally narrower than lower portion 114 as viewed from either side and from the front or back compared to lower portion 114. Member 40 steps inwardly from the top of lower portion 114 to the bottom of upper portion 116 at a square annular upwardly facing ledge 118. Lower portion 114 includes substantially flat vertical parallel front and back walls 120 and 122, and substantially flat vertical parallel left and right side walls 124A and 124B which are perpendicular to front and back walls 120 and 122. The front edges of side walls 124A and B are rigidly secured respectively to the left and right edges of front wall 120 at respective corners. Likewise, the rear edges of left and right side walls 124A and B are rigidly secured to the left and right edges of back wall 122 at respective corners. Upper portion 116 likewise includes front, back and left and right flat vertical side walls which are rigidly secured to and extend upwardly from ledge 118 to a horizontal square flat top wall serving as the top of button 116.

The front and back walls and side walls of the upper and lower portions 114 and 116 define there within a cavity 126 which is closed at the top by the top wall of button 116 and has a bottom entrance opening 128 and a front entrance opening 130 which communicate with one another. The bottom entrance opening 128 and front entrance opening 130 may also be thought of as a single entrance opening which generally opens downwardly and forward. Back wall 132 has a bottom 132 which serves as the bottom of member 40. Front wall 120 has a bottom edge 134 which is substantially higher than bottom 132 and defines the top of front entrance opening 130. The lower portions of left and right side walls 124A and B have cam surfaces 136 running along the front edges thereof and extending from adjacent the bottom of the respective side walls and adjacent the bottom 132 of back wall 122 and angling forward and upward therefrom to respective upper ends 136 which are adjacent and spaced downwardly from bottom 134 of front wall 120. Upper front edges 138 are also positioned forward of the bottom of wall 120 in the exemplary embodiment.

Actuating member 40 further includes an L-shaped switch-engaging member 140 which is cantilevered from a lower end thereof and extends upwardly therefrom. Member 140 includes a horizontal shorter leg 141 which is rigidly secured at its rear end to front wall 120 and extends forward therefrom to a forward end to which a lower end of a longer vertical leg 142 is rigidly secured. Longer leg 142 extends upwardly to a top terminal end 144. Leg 142 is thus spaced forward of front wall 120 and the front wall of upper portion 116 by a space 146 which opens upwardly and also to the left and right. As shown in FIG. 3, the back wall 92 is received in space 146. Likewise, the back of wall 58 above shelf 64 and adjacent top edge 60 is received in space 146. Leg 142 is received in and extends through holes 70 and 109 in the secured position shown in FIG. 5.

A plurality of one-way ratchet teeth or locking teeth 148 (FIG. 3) are formed integrally with and extend rearwardly from back wall 122 of lower portion 114. Teeth 148 are vertically spaced from one another and adjacent one another. In the exemplary embodiment, there are multiple teeth 148 to facilitate locking actuating member 40 in one of multiple positions associated with securing device 1 to various sizes of bottle necks. Typically, there are at least five or ten teeth 148 and in the exemplary embodiment, at least fifteen, twenty, or twenty-five teeth.

Locking teeth 148 are part of a locking mechanism for securing actuating member 40, catch member 42, blocking member 44, arms 48 and the associated components in a selected secured or securing position for securing device 1 to the bottle neck, as shown in FIG. 5. The locking mechanism includes a locking device for engaging teeth 148 to selectively lock member 40. In particular, the locking mechanism includes a flat vertical spring plate 150 which is rigidly secured to the front or inner surface of back wall 84 of housing 18. The locking mechanism further includes a pair of spring biased tines 152 each of which is respectively cantilevered from an upper end rigidly secured to plate 150 and which angles downwardly and forward therefrom to a lower bent end 154 which angles more sharply forward to a terminal forward lower end. Bent ends 154 are configured to be received within the spaces between teeth 148 and thus engage a respective locking tooth 148. Plate 150 and tines 152 are formed of a single piece of spring metal which is magnetically attractable. The lower terminal ends 154 are movable back and forth in forward and rearward directions indicated at Arrows A by a pivotal movement of each tine 152 adjacent its secured end at its intersection with plate 150. Tines 152 are spring biased to the locked position in which they engage teeth 148 and may be moved to the rearward unlocked position by a magnet placed adjacent the back of back wall 84 typically behind the free ends 154.

With continued reference to FIGS. 2B and 3, cam or catch member 42 has a lower section which includes a central portion 156 and left and right wings 158A and 158B which are rigidly secured to and extend respectively to the left and right from the left and right sides of central portion 156. Member 42 further includes a head or catch 160 which is rigidly secured to and extends upwardly and forward from the top of central portion 156. Left and right wings 158A and 158B extend respectively to the left and right and then downwardly to form bottom terminal ends whereby the lower portions of the wings and central portion 156 define therebetween left and right guide slots 161 which extend from the front to the back of member 42. Slots 161 open downwardly, forward and rearward and are closed at the top. Central portion 156 defines a spring-receiving hole 162 which extends from the front surface thereof rearwardly to a back wall of the central portion defining a forward facing spring engaging surface 164 (FIG. 3). Head or catch 160 extends upwardly and forward to an upper forward terminal end which serves as a bottle neck-engaging portion including a forward facing neck portion engaging surface 166 at the front of the catch and an upwardly facing flange-engaging surface 168 extending rearwardly from the front of the catch. Cam member 42 further includes left and right cam surfaces 170A and 170B which are formed along the upper back portion of central portion 156 and/or wings 158. Each cam surface 170 angles upwardly and forward and faces upwardly and rearwardly. Cam surfaces 170 are configured to slidingly engage the respective left and right cam surfaces 136 of actuating member 40. As shown in FIG. 3, central portion 156 has a downwardly facing convexly curved bottom surface 172 as viewed from the left side or the right side. Surface 172 is generally semi-circular so that a forward portion thereof faces downwardly and forward and a rearward portion thereof faces downwardly and rearwardly.

With primary reference to FIGS. 2B and 3, blocking member 44 includes a front section 174 and a rear section 176 rigidly secured to the back of front section 174 and extend rearwardly therefrom. Member 44 defines a pair of bottom slots 177 which are straight and parallel to one another and extend from the front to the rear of the bottom of member 44. Front section 174 has a forward-facing bottle neck-engaging surface 178 which is concavely curved as viewed from above. The left and right sides of front section 174 define left and right blocking arm-receiving and spring-receiving cavities 180A and 180B which communicate with surface 178 along the left and right sides thereof. Left cavity 180A opens forward and to the left. Right cavity 180B opens forward and to the right. Front section 174 defines upper and lower hinge pin holes on the left and right sides whereby the left holes communicate with left cavity 180A and the right holes communicate with cavity 180B. Holes 182 receive therein the typically metal hinge pins 50A and 50B.

Rear section 176 defines a central slide channel 184 which opens upwardly and rearwardly, and which is bounded at the front by front section 174 and at the bottom by a flat horizontal bottom wall of the rear section. Rear section 176 further defines left and right pockets 186 which open upwardly and are positioned to the left and right of channel 184 respectively and spaced therefrom by parallel vertical wall or guides 188 which are elongated from front to back. Slide channel 184 receives therein the lower part of central portion 156 of catch member 42 with bottom surface 172 engaging and resting on the upwardly facing surface of the bottom wall of channel 184. Pockets 186A and 186B receive respectively therein the lower ends of the left and right wings 158A and 158B of member 42. Guide slots 161 of member 42 receive therein guides 188 respectively. Rear section 176 has a rear surface 190 which is convexly curved as viewed from above and which meets a concavely curved forward-facing inner surface of housing 18. The back of front section 174 defines a central spring-receiving cavity which communicates with channel 184 and is bounded by a rearwardly facing spring-engaging surface 192.

Compression spring 46 is received within channel 84 and the spring-receiving cavities so that the rear end of spring 46 abuts surface 164 and the front end of spring 46 abuts surface 192. Spring 46 is always at least partially compressed to provide a constant spring bias of catch member 42 rearwardly relative to blocking member 44 and likewise a spring bias of blocking member 44 forward relative to catch member 42. Each of catch member 42 and blocking member 44 is moveable forward and rearwardly in a liner manner relative to one another as indicated at Arrow B in FIG. 3. In addition, when spring 46 is not fully compressed and/or not sufficiently compressed to allow blocking member 44 and actuating member 46 to tightly clamp cam member 42 therebetween, catch member 42 is also pivotable relative to blocking member 44 and the other components of device 1 so that head 160 and thus the bottle-engaging portion thereof is able to pivot upwardly and downwardly to a limited degree as well as forward and rearward to a limited degree as indicated at Arrow C in FIG. 3. In the exemplary embodiment, member 42 is not pivotally connected to blocking member 44 by a hinge pin and thus is not limited to pivoting about a single horizontal left-to-right axis. Rather, catch member 42 is able to pivot loosely respectively about a plurality of parallel horizontal left-to-right axes depending upon the relative positions of catch member 42 and blocking member 44 relative to one another and relative to base 14. Thus, member 42 is pivotable when located at multiple positions, including in the unlocked position (FIG. 3), in the locked position (FIG. 5) under the conditions noted above, and in multiple positions therebetween.

The pivotal movement of catch member 42 may also be described as a rocking movement in which downwardly facing convexly curved bottom surface 172 may rock forward and rearward on the upwardly facing surface of the horizontal bottom wall of channel 184. Catch member 42 is thus capable of forward and rearward back and forth rocking movement with rocking surface 172 rockingly engaging said upwardly facing surface. Channel 184 may thus also be referred to as a rocking channel in which member 42 can rock. Surface 172 slidably engages the upwardly facing surface of the horizontal bottom wall of channel 184 during linear forward and linear rearward movement of one of catch member 42 and blocking member 44 relative to the other. When spring 46 is fully or sufficiently compressed, front portion 174 of blocking member 44 and cam surfaces 136 of actuating member 40 securely clamp member 42 therebetween so that member 42 is substantially immobilized and thus unable to pivot or rock.

With continued reference to FIGS. 2B and 3, blocking arms 48 have a front 194 and a back 196. Front 194 serves as a free or terminal end of the respective arm. Each arm 48 adjacent back 196 defines a pair of hinge pin holes 198. Each arm 48 has a substantially horizontal upwardly-facing top surface 205 extending from adjacent front 194 to adjacent back 196. Each arm 48 also has a substantially horizontal downwardly-facing bottom surface 207 likewise extending from adjacent front 194 to adjacent back 196. Each arm has an outer surface 200 and an inner surface 202. The outer surface 200 of left arm 48A is the left or leftward-facing surface while the inner surface 202 thereof is the right or rightward-facing surface. The outer surface 200 of right arm 48B is the right or rightward-facing surface while the inner surface 202 thereof is the left or leftward facing surface. In the exemplary embodiment as viewed from above, the outer surfaces 200 are convexly curved adjacent front ends 194 and include a substantially straight portion extending from the convexly curved front portion thereof to adjacent the back ends of the arms. As viewed from above, a front portion 204 of each arm is narrower than a rear portion 206 thereof. More particularly, each arm tapers to become gradually wider moving in the rearward direction. As shown in FIG. 4, the rear ends 196 of arms 48A and 48B are respectively received within left and right cavities 180A and 180B of blocking member 44. The left and right hinge pins 50A and 50B are received respectively through the holes 198 in the left and right arms 48A and 48B to pivotally mount the blocking arms upon blocking member 44 with the blocking arms extending forward of the front of the blocking member to the respective free ends 194 thereof. Arms 48 are respectively mounted in cantilever fashion on blocking member 44 by hinge pins 50.

Referring to FIG. 2B, each torsion spring 52 has a coil 208 with first and second lever arms 210 and 212 connected to and extending outwardly from the opposite ends of the coil. When assembled, the coil 208 of each torsion spring 52 is received between the upper and lower portions of rear portion 206 with first arm 210 engaging a forward-facing surface of the front section 174 of blocking member 44 adjacent surface 178 and the second arm 212 engaging the inner surface 202 of the given arm 48. The corresponding hinge pin 50 passes through coil 208 in order to secure the spring 52 in place. The given lever arm 212 presses outwardly against inner surface 202 to provide a spring bias of the front end 194 of arm 48 outwardly away from vertical center line CL of sleeve cavity 20. Thus, the front end 194 of left arm 48A is biased to the left whereas the front 194 of right arm 48B is biased toward the right and thus the front ends 194 of the left and right arms 48 are biased away from one another.

With primary reference to FIG. 2C, insert 56 is an annular generally oval structure formed of a relatively thin continuous wall having a top edge 214 and a bottom edge 216. Insert 56 includes an arcuate front wall segment 218, an arcuate back wall segment 220, and straight left and right side wall segments 222A and 222B. Front wall segment 218 is in the exemplary embodiment semi-circular as viewed from above and includes an inner or rear slide or cam surface 224 which is concavely curved and semi-circular as viewed from above. In the exemplary embodiment, inner surface 224 has a radius of curvature which is substantially the same as that of the convexly curved front portions of the outer surfaces 200 of blocking arms 48 which extend from front ends 194 rearwardly to the straight portions of outer surfaces 200. Side walls 222 each have straight inner surfaces 226 which are parallel to one another and extend rearwardly from the opposed curved ends of arcuate surface 224. Back wall 220 has a cutout 228 extending downwardly from top edge 214 part way to bottom edge 216 whereby back wall 220 includes a central shorter back wall portion 230 which is shorter than the remaining portions of back wall segment 220 and the front and side wall segments. In the secured position of the securing mechanism and as shown in FIG. 4, the straight portions of the outer surfaces 200 of blocking arms 48 abut or are closely adjacent the straight inner surfaces 226 of insert 56, and the convexly curved portions of the outer surfaces 200 adjacent front ends 194 of blocking arms 48 abut or are closely adjacent the concavely curved inner surface 224 of insert 56. In the unsecured position in which actuating member 40 is in its fully raised position (FIGS. 3, 7), blocking member 44 is in its rearmost position abutting a forward facing surface of housing 18, such as the front surface of back wall segment 220 of insert 56, which serves as a stop whereby blocking member 44 can move rearwardly no further. In this position, cam member 42 is biased rearwardly to its rearmost position by spring 46.

With continued primary reference to FIG. 2C, bottom member 154 includes a sleeve bottom cylindrical side wall 232 which can also be referred to as an entrance opening side wall which forms the bottom portion of sleeve 16 and thus defines the bottom entrance opening thereof. In the exemplary embodiment, side wall 232 includes a taller front portion 234 which is semi-circular as viewed from above and has a semi-circular top surface or upwardly facing ledge 236 which is directly below the semi-circular bottom or ledge 62 of side wall 58 when assembled (FIG. 3). Side wall 232 is within a front or sleeve portion of member 54, which also includes a rear or housing section 238 which includes a substantially horizontal flat bottom wall 240 which closes the bottom of housing 18. A generally oval lip 242 forms an outer perimeter around the entire member 54 and has the same shape as the bottom of skirt side wall 74 to which it is rigidly secured. Rear section 238 further includes left and right guide walls 244 which are straight and parallel to one another. Walls 244 are rigidly secured to and extend upwardly from the top of bottom wall 240 to horizontal top edges on which blocking member 44 is slidably seated in order to slide forward and rearward thereon. More particularly, slide walls 244 are received respectively within slots 177 whereby the tops of walls 244 slidably engage the slots during movement of member 44 forward and rearwardly, such that guide walls 244 and slots 177 ensure linear sliding movement of member 44. As shown in FIG. 3, arcuate back surface 224 of front wall segment 218 of insert 56, downwardly facing ledge 62 of sleeve side wall 58 and upwardly facing ledge 236 of bottom side wall segment 232 define an arcuate slide channel 246 which is horizontal as viewed from the side (FIG. 3) and is semicircular as viewed from above (FIG. 4).

Figure 6:
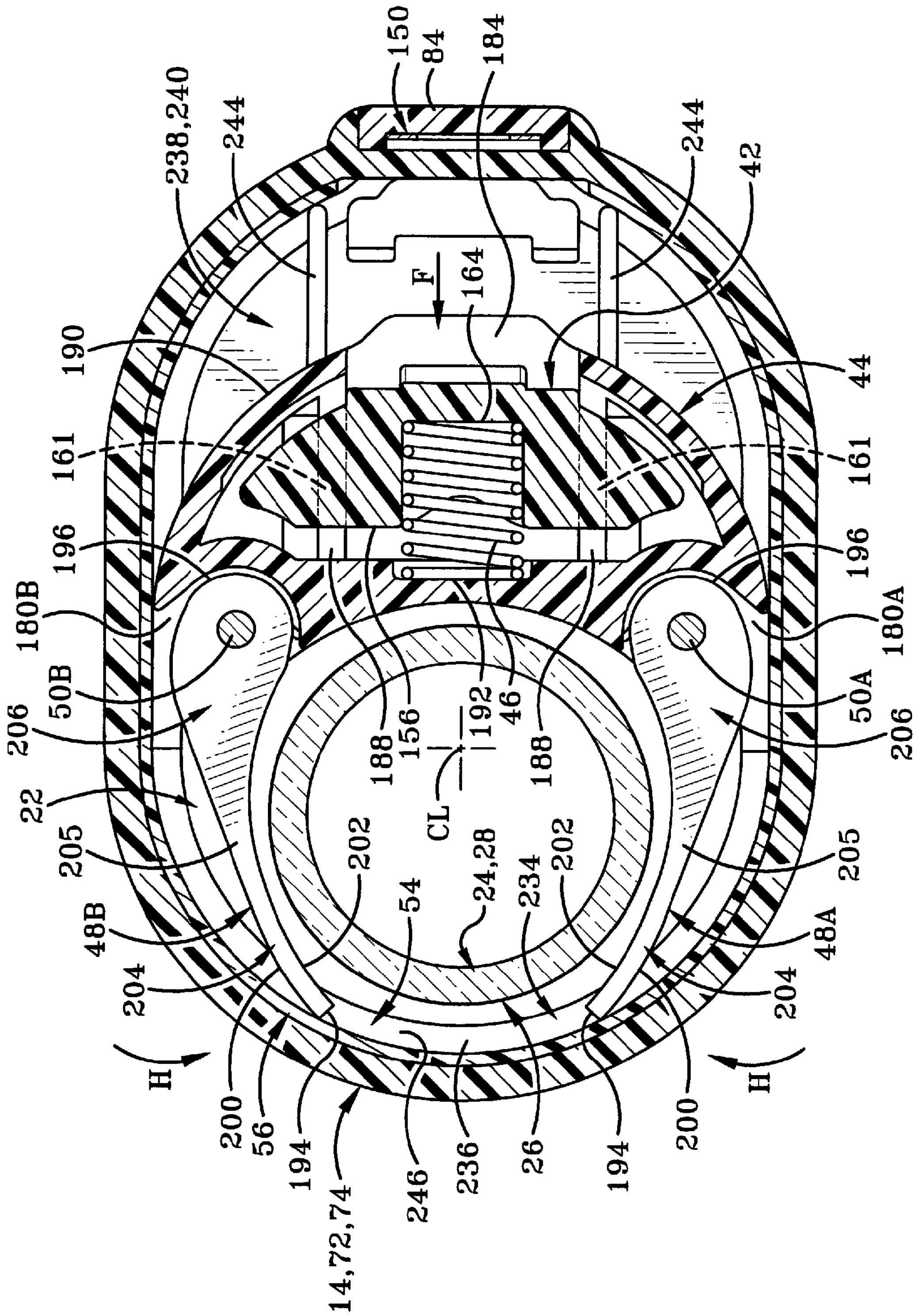
FIG. 6 is a sectional view taken on line 6-6 of FIG. 5.
Figure 7:
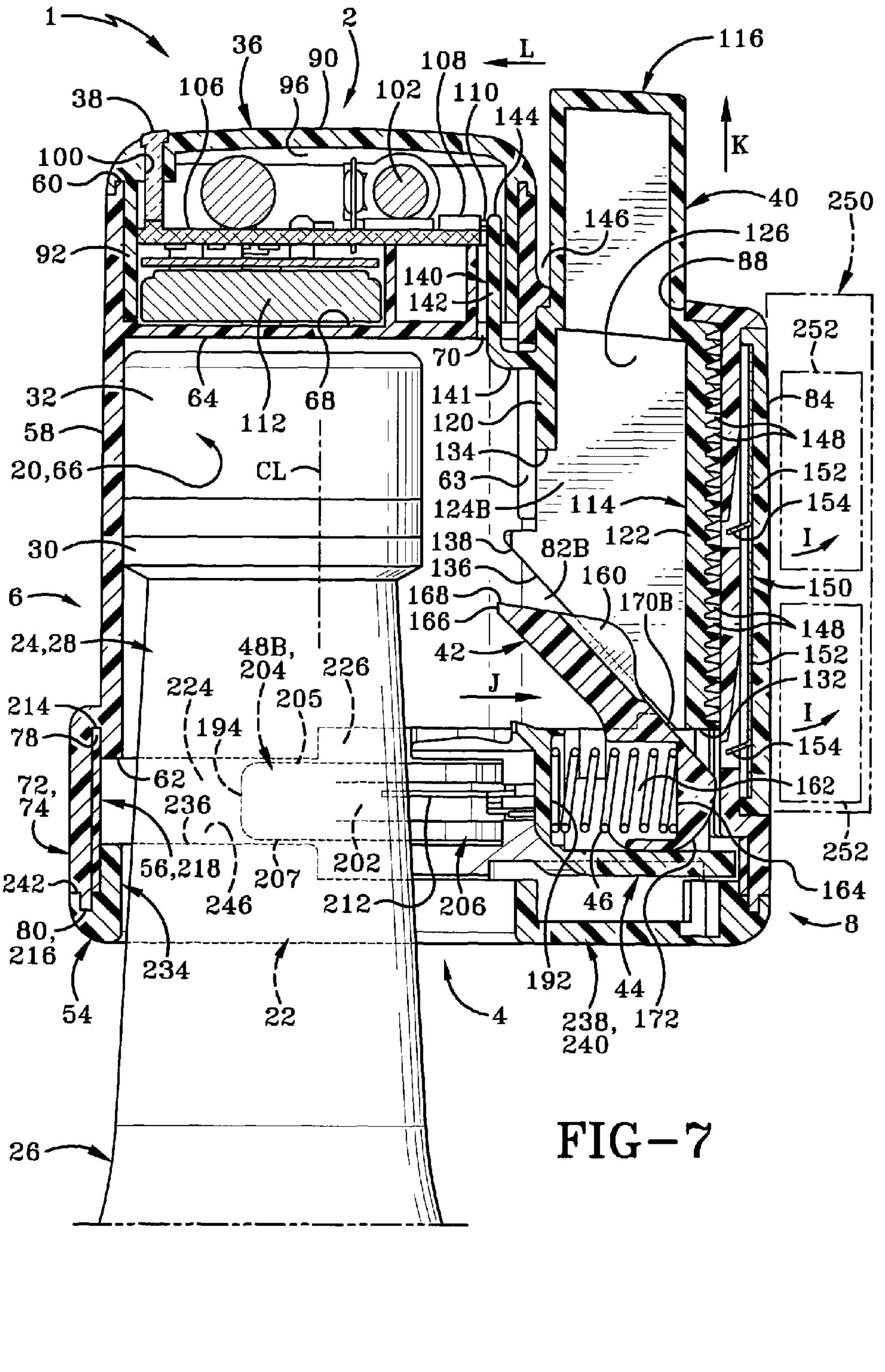
FIG. 7 is similar to FIG. 3 and shows a magnetic key having unlocked the locking mechanism to allow the securing mechanism to move from the secured position to the unsecured position.

Operation of device 1 is now described with primary reference to FIGS. 5-7. While device 1 is in the unsecured or released position of FIG. 3, bottleneck 24 is inserted into cavity 20 so that flange 30 is higher than the top front portion 168 of catch member 42. The user then manually engages and applies a downward force on button to depress button 116 of actuating member 40 to force member 40 vertically downwardly (Arrow D in FIG. 5) relative to base 14. In the exemplary embodiment, actuating member 40 moves in a linear, non-pivoting fashion. Switch engaging member 140 of member 40 thus moves downwardly as well whereby leg 142 thereof moves downwardly within hole 70 and disengages from switch arm 110, which is spring biased to move (Arrow E in FIG. 5) from the disarmed position thereof (FIG. 3) to the armed position thereof (FIG. 5) whereby the onboard alarm changes from a disarmed state to an armed state. When this change from the disarmed to the armed state occurs, the light (typically an LED) of alarm system 39 is turned on and shines through light pipe 38 to provide an externally visible and typically blinking signal that device 1 is armed. The onboard alarm is armed during the initial movement of member 40 downwardly. As the user continues to depress button 116 further downwardly, leg 142 may be removed entirely from upper cavity 68 into lower cavity 66 via opening 70. As actuating member 40 moves downwardly, the free bent ends 154 of locking tines 152 move forwardly and rearward (Arrows A in FIG. 5) as the various teeth 148 push them rearwardly and the recesses between the teeth allow the forward-biased ends 154 to move forward in alternating fashion. Once actuating member 40 moves downwardly sufficiently to reach its secured position (varies depending on the size of the bottle neck) and thus move all members of the securing mechanism from respective unsecured or home positions to respective securing positions, end 154 of each locking tine 152 engages a respective locking tooth 148 in a locked position of the locking mechanism to lock actuating member 40 and all other securing members in the secured position.

In addition, the downward movement of actuating member 40 results in the substantially horizontal forward movement (Arrow F in FIG. 5) of cam member 42, blocking member 44, spring 46, blocking arms 48, hinge pins 50 and springs 52, which move forward together as a unit substantially perpendicular to the movement of actuating member 40. More particularly, cam surfaces 136 slidingly engage cam surfaces 170 during the downward movement of operating member 40 to translate this downward movement to forward movement of cam member 42 and the other components previously mentioned. The forward movement of cam member 42 is translated to blocking member 44 via spring 46. During the forward movement of cam member 42, neck engaging surface 166 moves from a position out of contact with neck portion 28 to the position in contact with neck portion 28, at which time surface 166 slides upwardly along the outer surface of neck portion 28, causing the upper front portion of cam member 42 to pivot (Arrow G in FIG. 5) rearwardly and upwardly as the lower portion of cam member 42 continues forward movement in response to the urging of the engagement between the cam surfaces 136 and 170. Ultimately, catch member 42 moves forward far enough to reach the secured position in which bottle neck 24 is clamped securely between the rearwardly facing front inner surface of sidewall 58 and the neck engaging portion of catch member 42, thus preventing removal of bottle neck from sleeve cavity 20 or removal of device 1 from the bottle neck.

Furthermore, the forward movement of blocking member 44 in response to the downward movement of actuating member 40 from the unsecured position to the secured position results in neck engaging surface 178 moving from a position (FIGS. 3, 7) out of contact with neck portion 28 into a position (FIG. 5) in contact therewith. As additional force is applied downwardly on button 116 of member 40, the lower portion of cam member 42 which engages spring 46 continues to move forward, thus compressing spring 46 between the engaging surfaces 164 and 192 until bottleneck 28 is clamped between surface 178 of blocking member 44 and the front rearwardly facing inner surface of sleeve 16 whereby blocking member 44 stops moving forward. In the secured position, blocking member 44 remains directly below catch member 42 and fills a substantial portion of cavity 20 adjacent bottom entrance opening 22 and rearward of bottle neck portion 28. In the secured position, blocking member 44 is either fixed relative to base 14 and the other components of device 1 or may be slidable rearwardly to a limited degree if sufficient rearward force is applied to member 44 to overcome the spring bias of mostly compressed spring 46.

Moreover, the forward movement of the various components noted above with reference to Arrow F includes blocking arms 48A and 48B. This forward movement of arms 48 results in the pivotal movement thereof (Arrows H in FIG. 6) about hinge pins 50 respectively. More particularly, the front ends 194 pivot toward one another. Thus, the front end 194 of left arm 48A pivots to the right while the front 194 of right arm 48B pivots to the left. More particularly, this is caused by a sliding camming engagement between arms 48 and slide surface 224. During the forward movement of the various components, each blocking arm 48 adjacent front end 194 thereof slidably engages surface 224, which serves as a cam surface causing the pivotal movement of arms 48 noted above or translates the forward movement of arms 48 into the pivotal movement or arms 48 noted above. Throughout this pivotal movement, the front ends 194 or the sliding surfaces of arms 48 which slidingly engage slide surface 224 remain at a constant distance from centerline CL because surface 224 is concentric about centerline CL. However, the portion of each arm 48 extending from its pivot pin 50 to its front end 194 or its sliding surface moves toward centerline CL as the arm pivots during forward movement of arms 48.

In the secured and locked position shown in FIGS. 5 and 6, surfaces 166 and 168 thus respectively engage neck portion 28 and a downwardly facing portion of flange 30 to secure device 1 on the bottle whereby device 1 cannot be removed from the bottleneck without the proper key or without damage to device 1 or bottle 26. In the secured and locked position, surface 178 typically engages that portion 28 and inner surfaces 202 of arms 48 are in contact with or closely adjacent the outer surface of neck portion 28 on opposed sides thereof (FIG. 6). In the secured and locked position, outer surfaces 200 (except for the slide surface thereof which slides along slide surface 224) are out of contact with curved surface 224 and straight surfaces 226 of insert 56, a large portion of each arm 48 is within sleeve cavity 20, and the straight portion of each outer surface 200 may be spaced radially inwardly of the circular inner surface of sleeve bottom sidewall 232 (that is, closer to centerline CL than said circular inner surface). In the secured position, blocking member 44 and blocking arms 48 help to block access to catch member 42 via entrance opening 22, thus making it more difficult for a potential thief to insert a screwdriver or other object through entrance opening 22 upwardly into cavity 20 to tamper with catch member 42 and thus damage or dislodge it from the secured position.

In the secured position (and also in the unsecured position), top surface 205 of each arm 48 is in contact with or closely adjacent ledge 62, and bottom edge 207 is closely adjacent or in contact with ledge 236. Thus, in the secured position, ledge 62 makes it more difficult to dislodge or break arm 48 inasmuch as upward force on arm 48 especially adjacent ledge 194 is countered by ledge 62 whereby ledge 62 effectively does not allow any upward movement of outer end 194, or allows only a very small degree of upward movement of the outer end 194 due to abutment of top edge 205 with ledge 62. Similarly, downward force applied to arm 48 especially adjacent end 194 is countered by an engagement between bottom edge 207 and ledge 236 whereby ledge 236 likewise allows little or no downward movement of outer end 194. Upper and lower edges 205 and 207 of each arm 48 may slidably engage ledges 62 and 236 respectively during movement between the secured and unsecured positions.

When an authorized user desires to remove security device 1 from a given bottle neck 24, a magnetic key 250 is positioned against or adjacent the rear surface of back wall 84 of housing 18, as shown in FIG. 7. More particularly, key 250 typically includes a pair of magnets which are aligned directly behind ends 154 of tines 152 to magnetically attract ends 154 rearwardly (Arrows I) out of engagement with teeth 148 to unlock the locking mechanism. Once in the unlocked position, the securing mechanism automatically moves from the secured position of FIGS. 5 and 6 to the unsecured position shown in FIG. 7, thus reversing all the movement of the various components of device 1 associated with moving device 1 from the unsecured position to the secured position. This automatic movement from the secured to the unsecured position is driven by the spring bias of blocking arm springs 52, each of which applies a force on the respective blocking arm 48 away from centerline CL and causes the front ends 194 to move away from one another (opposite Arrows H in FIG. 6). This spring force of springs 52 thus forces the sliding surfaces of arms 48 adjacent front ends 194 to slide outwardly and rearwardly along cam surface 224 of insert 56, thus translating the pivotal movement of arms 48 into rearward movement (Arrow J in FIG. 7) of various components of the securing mechanism including catch member 42, blocking member 44, spring 46, blocking arms 48, pins 50 and springs 52. As shown in FIG. 7, this rearward movement is translated by a sliding engagement of cam surfaces 170 with cam surfaces 136 into upward movement of operating member 40 (Arrow K) to its highest or fully raised home position so that arm 142 engages and depresses switch arm 110 (Arrow L) to move the onboard alarm from the armed to the disarmed state. The upward movement of member 40 is stopped by engagement of ledge 118 with the bottom surface of top wall 86, which serves as a stop.

Device 1 is typically used as part of a security system including a security gate within a store or the like. EAS tag 102 is configured to be sensed by the security gate when device 1/EAS tag 102 comes within a predetermined distance (typically a few feet) of an appropriate sensor of the security gate. In addition, the onboard alarm includes an onboard sensor which typically senses when device 1 is within a similar predetermined distance from the security gate. Thus, when a thief carries bottle 26 with device 1 secured thereon in the armed state within the predetermined distance, the sensor produces a signal to cause the speaker of the onboard alarm to emit a loud attention-getting sound. The alarming sound is directed outwardly in opposite directions from opposed sides of device 1 via the sound exit openings 98 and sound exit opening 22. When bottle 26 and device 1 are in their upright positions, the alarming sound is thus directed upwardly via openings 98 and downwardly via opening 22. The configuration of device 1 to direct or emit the alarm sound in different directions makes it more difficult for a thief to muffle the sound of the alarm by covering one or more sound exit openings with a hand, for example. Providing the sound exit openings in substantially different areas thus requires the thief to use, for example, one hand to cover one sound exit opening (or set thereof) and another hand to cover the other sound exit opening (or set thereof). Furthermore, covering the bottom opening 22 sufficiently to significantly muffle the alarm sound is in itself difficult.

A security device similar to device 1 may be formed without the onboard alarm and thus also without the structure (such as wall 64) which forms the upper cavity in which the onboard alarm is disposed. Such a device typically will retain an EAS tag, which may be positioned in various locations. In addition, such a device may be formed so that the top cover or member and primary member are molded as a single piece.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

The invention claimed is:

1. A bottle security device comprising:

a base having a top and bottom and defining a cavity having a bottom entrance opening; the cavity adapted to receive a bottle neck through the bottom entrance opening;

a first member mounted on and movable forward and rearward relative to the base; and a first arm which is pivotally mounted on and extends forward from the first member to a front end which is movable leftward and rightward.

2. The bottle security device of claim 1 wherein the cavity has a vertical centerline; and the front end of the first arm is spring biased away from the vertical centerline.

3. The bottle security device of claim 1 wherein the first arm pivots in response to movement of the first member.

4. The bottle security device of claim 1 wherein the first member moves in response to pivotal movement of the first arm.

5. The bottle security device of claim 1 wherein the entire first member and the entire first arm move rearwardly in response to pivotal movement of the first arm.

6. The bottle security device of claim 1 further comprising a sliding engagement between the first arm and base during pivotal movement of the first arm.

7. The bottle security device of claim 6 wherein the sliding engagement causes the first arm to pivot.

8. The bottle security device of claim 6 wherein pivotal movement of first arm causes the sliding engagement.

9. The bottle security device of claim 6 further comprising an arcuate slide surface of the base;

wherein the sliding engagement is between the first arm and the arcuate slide surface.

10. The bottle security device of claim 6 further comprising a slide surface of the base;

a slide surface of the first arm adjacent the front end of the first arm;

a pivot about which the first arm is pivotally mounted on the first member;

an outer surface of the first arm which extends rearwardly from adjacent the front end of the first arm to adjacent the pivot;

a first position of the first arm in which the outer surface from adjacent the front end of the first arm to adjacent the pivot is closely adjacent or in contact with the slide surface of the base;

a second position of the first arm in which, except for the slide surface of the first arm, the outer surface of the first arm is out of contact with and spaced inwardly from the slide surface of the base;

wherein the sliding engagement is between the slide surface of the first arm and the slide surface of the base.

11. The bottle security device of claim 1 wherein the base comprises a sleeve sidewall which defines the cavity;

the sleeve sidewall has an arcuate inner surface which is concavely curved as viewed from above, a downwardly facing surface which extends inwardly from the arcuate inner surface, and an upwardly facing surface which extends inwardly from the arcuate inner surface so that the arcuate inner surface, the downwardly facing surface and the upwardly facing surface define a channel;

wherein the first arm slides within the channel during pivoting movement of the first arm.

12. The bottle security device of claim 11 further comprising an upwardly facing surface of the first arm which is engageable with the downwardly facing surface.

13. The bottle security device of claim 1 further comprising a securing mechanism having a securing position adapted to secure the device to the bottle and an unsecured position adapted to allow the device to be removed from the bottle;

wherein the securing mechanism moves from the secured position to the unsecured position in response to pivotal movement of the arm.

14. The bottle security device of claim 1 further comprising a second arm which is pivotally mounted on and extends forward from the first member to a front end which is movable leftward and rightward.

15. The bottle security device of claim 1 further comprising an electrical circuit which opens or closes in response to pivotal movement of the first arm.

16. The bottle security device of claim 1 further comprising an actuating member; and an electrical circuit;

wherein the electrical circuit opens or closes and the first arm pivots in response to movement of the actuating member.

17. The bottle security device of claim 1 further comprising an onboard audible alarm.

18. The bottle security device of claim 17 further comprising an actuating member;

wherein the alarm changes from a disarmed state to an armed state and the first arm pivots in response to movement of the actuating member.

19. The bottle security device of claim 17 wherein the alarm changes from an armed state to a disarmed state in response to pivotal movement of the first arm.

20. The bottle security device of claim 1 wherein the first member has an engaged position adapted to engage the bottle neck and a disengaged position adapted to be disengaged from the bottle neck.

21. The bottle security device of claim 20 further comprising a second member mounted on the base and movable between an engaged position adapted to engage the bottle neck and a disengaged position adapted to be disengaged from the bottle neck; the second member being movable relative to the first member;

an upwardly facing surface of the first member;

a downwardly facing surface of the second member; and an engagement between the upwardly facing surface and downwardly facing surface.

22. The bottle security device of claim 20 further comprising a second member mounted on the base and movable between an engaged position adapted to engage the bottle neck and a disengaged position adapted to be disengaged from the bottle neck; the second member being movable relative to the first member; and a spring which extends from the first member to the second member.

23. The bottle security device of claim 1 wherein the first member moves linearly forward and rearward relative to the base; and the first arm is pivotally mounted on the first member so that the first arm moves forward and rearward with the first member relative to the base.

24. The bottle security device of claim 6 wherein the sliding engagement is between the front end of the first arm and the base.

25. The bottle security device of claim 9 wherein the cavity has a vertical centerline; and the arcuate inner surface is concentric about the centerline.

26. The bottle security device of claim 14 wherein the first arm is pivotally mounted on the first member about a first axis; and the second arm is pivotally mounted on the first member about a second different axis.

27. The bottle security device of claim 14 wherein the front end of the left arm is spring biased to the left; and the front end of the right arm is spring biased to the right.

28. A security device comprising:

a base defining a cavity having a bottom entrance opening; the cavity adapted to receive a bottle neck through the bottom entrance opening;

a catch member which is movably mounted on the base to move between an engaged position in which the catch member is adapted to engage the bottle neck and a disengaged position in which the catch member is adapted to be disengaged from the bottle neck;

a blocking member which is movably mounted on the base and which is below the catch member to help block access to the catch member from below in the engaged position; and a first arm pivotally mounted on the blocking member so that the first arm moves with the blocking member relative to the base;

wherein the catch member moves from the engaged position to the disengaged position in response to pivotal movement of the first arm.

29. The bottle security device of claim 28 wherein the catch member is movable linearly back and forth relative to the base.

30. The bottle security device of claim 28 further comprising a cam surface on the base;

a sliding surface on the first arm; and a spring which applies a force on the first arm to force the sliding surface of the first arm to slide along the cam surface, thus translating pivotal movement of the first arm into movement of the blocking member, first arm and spring relative to the base.

31. The bottle security device of claim 28 wherein the catch member is able to pivot relative to the base respectively about a plurality of parallel axes.

32. A bottle security device comprising:

a base defining a cavity having a bottom entrance opening; the cavity adapted to receive a bottle neck through the bottom entrance opening;

a first member mounted on the base and movable between a first member engaged position adapted to engage the bottle neck and a first member disengaged position adapted to be disengaged from the bottle neck;

a second member mounted on the base and movable between a second member engaged position adapted to engage the bottle neck and a second member disengaged position adapted to be disengaged from the bottle neck; the second member being movable relative to the first member;

an upwardly facing surface of the second member;

a downwardly facing surface of the first member; and an engagement between the upwardly facing surface and downwardly facing surface;

wherein the engagement is a rocking engagement such that the first member is capable of back and forth rocking movement with the downwardly facing surface rockingly engaging the upwardly facing surface.

33. The bottle security device of claim 32 wherein the first member is linearly movable relative to the second member.

34. The bottle security device of claim 33 wherein the downwardly facing surface slidably engages the upwardly facing surface during linear movement of the first member relative to the second member.

* * * * *